United States Patent
Spartiotis et al.

(10) Patent No.: US 11,653,886 B2
(45) Date of Patent: May 23, 2023

(54) ULTRA-FAST SCANNING X-RAY IMAGING DEVICE

(71) Applicant: ATHLOS OY, Espoo (FI)

(72) Inventors: Konstantinos Spartiotis, Espoo (FI); Dimitrios Chatzistratis, Espoo (FI)

(73) Assignee: ATHLOS OY, Espoo (FI)

( * ) Notice: Subject to any disclaimer, the term of this patent is extended or adjusted under 35 U.S.C. 154(b) by 0 days.

(21) Appl. No.: 17/819,656

(22) Filed: Aug. 15, 2022

(65) Prior Publication Data

US 2022/0395239 A1  Dec. 15, 2022

Related U.S. Application Data (60) Division of application No. 17/071,468, filed on Oct. 15, 2020, now Pat. No. 11,559,267, which is a (Continued)

(30) Foreign Application Priority Data

Apr. 25, 2018  (FI) ................................. 20187059

(51) Int. Cl.
*A61B 6/00* (2006.01)
*A61B 6/14* (2006.01)

(52) U.S. Cl.
CPC .............. *A61B 6/14* (2013.01); *A61B 6/4078* (2013.01); *A61B 6/4085* (2013.01); (Continued)

(58) Field of Classification Search
CPC ......... G06T 11/005; G06T 2207/10116; G01T 1/247; A61B 2034/2065; A61B 6/56; (Continued)

(56) References Cited

U.S. PATENT DOCUMENTS

| 6,035,013 A | 3/2000 | Orava et al. |
| 2002/0070365 A1 | 6/2002 | Karellas |

(Continued)

FOREIGN PATENT DOCUMENTS

| CN | 104079847 A | 10/2014 |
| EP | 1 795 918 A2 | 6/2007 |
| WO | 2008/109565 A1 | 9/2008 |

OTHER PUBLICATIONS

Office Action issued in Finnish Parent Application No. 20187059 dated Dec. 13, 2018.
(Continued)

*Primary Examiner* — Don K Wong
(74) *Attorney, Agent, or Firm* — Nixon & Vanderhye (57) ABSTRACT

Disclosed is a linear array ultra-fast scanning x-ray imaging device. The linear array x-ray imaging device is single photon sensitive, operating in frame output mode and including a pixel array Application Specific Integrated Circuit including the readout pixel array. The ASIC includes digital control logic and sufficient memory to accumulate digital output frames in various modes of operation prior to output from the ASIC, permitting advanced imaging functionalities directly on the ASIC, while maintaining a dynamic range of 16 bits and single photon sensitivity. The effective or secondary frames output from the pixel array ASIC can be tagged with user provided external triggers synchronizing the effective frames to the x-ray beam energy and/or to the movement of the x-ray source or imaged object. This enables dual energy imaging and ultra-fast scanning, without complex and costly conventional photon counting x-ray imaging sensors. The system architecture is simpler and higher performance.

1 Claim, 8 Drawing Sheets

Related U.S. Application Data continuation-in-part of application No. PCT/FI2019/050325, filed on Apr. 23, 2019.

(52) U.S. Cl.
CPC .......... *A61B 6/4233* (2013.01); *A61B 6/4482* (2013.01); *A61B 6/466* (2013.01)

(58) Field of Classification Search
CPC ... A61B 5/7289; A61B 5/7292; A61B 5/7285; A61B 5/389; A61B 5/369; A61B 5/05; A61B 34/10; A61B 17/1703; A61B 2090/365; A61B 6/545; A61B 6/547; A61B 6/4266; A61B 6/4208; A61B 6/4021; A61B 6/4014; A61B 6/405; A61B 6/14; A61B 6/482; A61B 6/4417; A61B 6/4441; A61B 6/4233; A61B 6/5205; A61B 6/027; A61B 6/032; A61B 6/037
See application file for complete search history.

(56) References Cited

U.S. PATENT DOCUMENTS

| | | |
|---|---|---|
| 2002/0196170 A1 | 12/2002 | McIlrath |
| 2003/0169847 A1 | 9/2003 | Karellas et al. |
| 2006/0011853 A1 | 1/2006 | Spartiotis et al. |
| 2006/0203959 A1 | 9/2006 | Spartiotis et al. |
| 2008/0063139 A1 | 3/2008 | Pantsar et al. |
| 2008/0217545 A1 | 9/2008 | Liu et al. |
| 2009/0005679 A1 | 1/2009 | Dala-Krishna |
| 2009/0290680 A1 | 11/2009 | Tumer et al. |
| 2012/0280131 A1 | 11/2012 | Spartiotis et al. |
| 2013/0329854 A1 | 12/2013 | Spartiotis et al. |
| 2015/0305696 A1 | 10/2015 | Yamakawa et al. |
| 2017/0230596 A1 | 8/2017 | Colonero et al. |
| 2017/0230597 A1 | 8/2017 | Fahim et al. |
| 2018/0017685 A1 | 1/2018 | Cao |
| 2018/0113226 A1* | 4/2018 | Naot ..................... G01T 1/1642 |

OTHER PUBLICATIONS

Hromalik, M. S. et al., "The FGPA Pixel Array Detector," Nuclear Instruments and Methods in Physics Research 1 701 (2013) 7-16.
International Search Report for PCT/FI2019/050325 dated Jul. 15, 2019, 5 pages.
Spartiotis et al., "A CdTe real time X-ray imaging sensor and system", Nuclear Instruments and Methods in Physics Research A, vol. 527, Issue 3, Jul. 21, 2004, 9 pages.
Parent U.S. Appl. No. 17/071,468, filed Oct. 15, 2020.
U.S. Appl. No. 17/819,661, filed Aug. 15, 2022.
Search Report issued in Finnish Patent Application No. 20187059 dated Dec. 13, 2018.
Search Opinion and Supplementary Search Report issued in European Patent Application No. 19793066.2 dated Dec. 2, 2021.
Extended European Search Report issued in European Patent Application No. 22180415.6 dated Nov. 23, 2022.
Singh et al., "High-speed detector for time-resolved diffraction studies," Journal of Physics: Conference Series, 11th International Conference on Synchrotron Radiation Instrumentation (SRI 2012), 2013, vol. 425, pp. 1-5.
Dinapoli et al., "A new family of pixel detectors for high frame rate X-ray applications," Nuclear Instruments and Methods in Physics Research Section A, 2010, vol. 617, pp. 384-386.
Seino et al., "Pulsed Bias Voltage Shutdown to Suppress the Polarization Effect for a CdTe Radiation Detector," IEEE Transactions on Nuclear Science, vol. 55, No. 5, Oct. 2008, pp. 2770-2774.

* cited by examiner

ULTRA-FAST SCANNING X-RAY IMAGING DEVICE

CROSS REFERENCE TO RELATED APPLICATIONS

This application is a Divisional of application Ser. No. 17/071,468, filed on Oct. 15, 2020, which is a Continuation-in-Part of PCT/FI2019/050325, filed on Apr. 23, 2019, which claims priority to application Ser. No. 20/187,059, filed in Finland on Apr. 25, 2018, all of which are hereby expressly incorporated by reference into the present application.

FIELD OF THE INVENTION

The present invention relates to x-ray imaging devices and more specifically to x-ray imaging devices suitable for ultra-fast scan imaging for a variety of applications.

BACKGROUND OF THE INVENTION

This section illustrates useful background information without admission of any technique described herein representative of the state of the art.

A variety of x-ray imaging devices have been developed and have become available for x-ray imaging over the past twenty years. Such x-ray imaging devices utilize scintillator convertor such as CsI coupled to a Complementary Metal Oxide Semiconductor ("CMOS") readout application specific integrated circuit ("ASIC"). In this case the x-rays convert to visible or near visible light in the scintillator and thereafter produce an electronic signal on the photodiodes that exist on each pixel on the CMOS. Alternatively x-ray scanning imaging devices are of the direct conversion type where the x-ray convert directly to an electronic pulse inside the bulk of a semiconductor substrate. Such examples include detectors such as CdTe, CdZnTe, $HgI_2$, GaAs, Ge, Se, Si etc. The electric pulse is drifting under the influence of an electric field applied with a high voltage across the bulk. Typical high voltage values applied to create the electric field are from few tens of volts and up to 1,000 Volts or even higher. The high voltage polarity can be positive or negative depending if one wants to collect electrons or holes.

The x-ray scanning imaging devices operate in the so called Time Delay Integration mode ("TDI") for outputting the image line by line or in the so called frame output mode for outputting frames instead of lines, much like a video streaming device. To this date the vast majority of x-ray scan imaging devices produce at most 300 frames per second (300 fps) and up to 1,000 fps. This corresponds to a frame period of one millisecond and up to a few milliseconds. Faster frames rates if at all achievable have to be integrated then on an FPGA (Field Programmable Gate Array) for slowing down the data stream, since there are limitations on the maximum data stream rate attainable with today's giga bit internet protocols that are mostly used in x-ray imaging in dental, medical and industrial applications. Consequently the FPGA needs to be big and having a lot of resources, some of them peripheral, to handle the high data rate. This makes the x-ray imaging device more expensive, less flexible and consuming more power.

Additionally should the originally produced frames be transferred to a Personal Computer ("PC"), then they need to be stored in a non-destructive way on a memory for the purpose of further processing and image reconstruction. Such examples include panoramic multi-layer reconstruction or TDI reconstruction in dental, medical and industrial applications.

In certain prior art imaging devices and systems thereto the frames produced from a fast frame producing sensor are non-destructively stored in an external memory, for example on the computer. Emphasis is placed here on the prior art architecture where the frame are "non-destructively" stored and "accessed in any order" in "real time" with a high speed computer memory. Secondly by external memory we intend to mean and identify here any memory that is resident either on the computer and/or on the printed circuit board (including FPGAs and peripherals) associated with the CMOS imager. In prior art devices, emphasized is the need for a moderate frame rate (not too high and about 300 fps), the need for the imaging device not to produce too much data and above all the need to retain or maintain in a non-destructive way all the frames in the computer memory for later use.

As mentioned the problem with these prior art systems is that this principle works for up to 300 fps or maybe a bit higher than that, but there is no sensible way of transferring for example 5,000 fps or even 10,000 fps from the CMOS imager to the computer and then store and use the frames. On the other hand there are distinct and unique advantages of having a very high frame rate such as that the dynamic range of the CMOS imager increases with the frame rate.

A separate problem is the polarization and temporal behavior of CdTe detectors and CdZnTe detectors that are becoming popular due to their high sensitivity. However polarization introduces a time dependent calibration which makes these sensors difficult to operate. Even more severe is the issue when the CdTe-CMOS scanner operates at very high speeds and continuously. Prior art describes depolarizing switching high voltage circuitries. However the approach does not work when the imaging device is active continuously because the circuitry and solution suggested are too slow and hundreds of milliseconds are lost as dead time. Therefore in an inline inspection system the approach of switching on/off an HV for example every 10 seconds, 30 seconds or 1 minute would not work. Additionally when the HV on/off operation happens in such long time intervals, it means that the frames produced in between will have a temporal response. Almost each frame needs to be calibrated with a time dependent function. In other words the calibration needs to take into account that the frames have different gain characteristics from one another. This has been a big problem in the industry.

SUMMARY

It has been observed that it would be extremely desirable and a major advancement in the field of x-ray imaging scanning devices to have an ultra-fast scanning CMOS imager without the bottlenecks of the prior art and to do so in a cost efficient manner. Embodiments of the current invention provide for an ultra-fast scanning imaging device with the following features and advantages:

Scanning speeds of up to 100 cm/sec with 100 micro meter resolution

Frame rates of up to 10,000 frames per second (fps) with 100 micro meter resolution. Respectively this corresponds to frame periods of 100 micro seconds.

Digital control logic resident on the CMOS ASIC which not only offers digitization but also processes the digital pixel values and performs on-chip image processing including static frame modulation, dynamic frame modulation and time delay integration output. These advanced functionalities are achieved with the use of a suitable memory on-chip, i.e. resident on the same CMOS that comprises the imager.

In the case of direct conversion x-ray imaging ultra-fast scanners the possibility of continuous operation without temporal behavior of the individual frames used in the image reconstruction. This is achieved with a new type of switching high voltage circuitry and technique for very fast on/off operation of the high voltage and without (emphasis added) changing the polarity.

Furthermore, it would be enormously advantageous to tag the frames produced on the CMOS with an external trigger or an external pulse train whereby the external pulses (triggers) are provided by the system into which the imaging device is integrated and allow for very accurate synchronization between the frames produced of the imaging device and a system parameter. The system parameters can be one or more of a) position of the imaging device and/or the x-ray source and/or the object to be imaged, b) time stamps and c) the energy (kV) and intensity (mA) of the x-rays as determined by the settings on the x-ray source and generator. The accuracy of the tagging (synchronization) of the frames produced by the imaging device to external triggers, generated by the user or the system, can be as good as 25 nsec (twenty five nanoseconds).

Embodiments of the invention finds particular application in dental panoramic, dental cephalometry x-ray imaging and dental 3D imaging (cone beam or fan beam 3D), in medical x-ray scanning and in industrial inline inspection, automatic x-ray inspection and industrial CT.

In accordance with a first aspect of the invention we provide an x-ray imaging device, comprising:
 a. a detector for detecting impinging x-rays and generating detector output signals;
 b. an application specific integrated circuit for receiving said detector output signals and comprising a readout pixel array and electronics for producing digital output pixel values corresponding to a frame period;
 wherein
 said application specific integrated circuit further comprises a digital memory for storing a resulting digital pixel value from accumulation or averaging of digital output pixel values from at least two frame periods prior to readout of said resulting digital pixel value from said application specific integrated circuit.

In certain embodiments, the said digital memory comprises one of a) SRAM, b) registers, c) FIFO, d) DRAM.

In certain embodiments, the said frame period is less than 1 millisecond.

In certain embodiments, the said frame period is less than 800 micro seconds.

In certain embodiments, the said frame period is less than 500 micro seconds.

In certain embodiments, the said frame period is less than 150 micro seconds.

In certain embodiments, the said digital memory accumulates or averages digital output pixel values from at least ten frame periods prior to readout from said application specific integrated circuit.

In certain embodiments, the said digital memory accumulates or averages digital output pixel values from at least twenty frame periods prior to readout from said application specific integrated circuit.

In certain embodiments, the said digital memory accumulates or averages digital output pixel values from at least two hundred frame periods prior to readout from said application specific integrated circuit.

In certain embodiments, the said application specific integrated circuit further comprises digital control electronics and said digital output pixel values are first shifted before accumulation or averaging on said digital memory prior to readout from said application specific integrated circuit and said application specific integrated circuit is outputting a time delay integration (TDI) stream of data.

In certain embodiments, the said detector is a direct conversion detector from the group of CdTe, CdZnTe, GaAs, Ge, HgI2, Si and Se.

In certain embodiments, the said CdTe is of the type with Al Schotky contacts on the pixel side.

In certain embodiments, the said x-ray imaging device also comprises a substrate containing electronics circuitry said electronics circuitry comprising a switching high voltage circuitry operable to depolarize said direct conversion detector, said switching high voltage circuitry operates to lower a high voltage applied to said direct conversion detector from an operational high voltage value to a low voltage value of the same polarity in periodic time intervals and for a very short period of time.

In certain embodiments, the said very short period of time is 1 millisecond, preferably 500 micro seconds, even more preferably 100 micro seconds and even more preferably 20 micro seconds or less.

In certain embodiments, the said periodic time interval is approximately every ten thousand frame periods, more preferably approximately every thousand frame periods, even more preferably every hundred frame periods and most preferably every frame period.

In accordance with the current invention or its embodiments we provide an x-ray imaging device capable of producing frames with a frame period of between 10 micro seconds to 20 milliseconds, said x-ray imaging device comprising a direct conversion radiation detector and a switching high voltage power supply operable to depolarize said direct conversion radiation detector said switching high voltage circuitry operates to lower a high voltage applied to said direct conversion detector from an operational high voltage value to a low voltage value of the same polarity wherein said low voltage supply of the same polarity lasts no longer than 1 millisecond and is applied on the detector in periodic time intervals.

In accordance with the current invention or its embodiments we provide an x-ray imaging device capable of producing frames with a frame period of between 10 micro seconds to 20 milliseconds, said x-ray imaging device comprising a direct conversion radiation detector and a switching high voltage power supply operable to depolarize said direct conversion radiation detector said switching high voltage circuitry operates to lower a high voltage applied to said direct conversion detector from an operational high voltage value towards a reference ground voltage wherein said ground voltage supply lasts no longer than 1 millisecond and is applied on the detector in periodic time intervals.

In accordance with yet another aspect of the invention we provide a linear array x-ray scanning imaging system comprising:
 a) one or more x-ray sources operable to produce selectively x-rays with a first and a second energy spectrum,
 b) a linear array x-ray imaging device operable to produce x-ray imaging frames wherein said linear array x-ray scanning imaging system produces a first trigger pulse synchronized with said first energy spectrum and a second trigger pulse synchronized with said second energy spectrum and said first and second trigger pulses are tagging said frames produced by the x-ray imaging device.

In accordance with yet another aspect of the invention we provide a linear array x-ray scanning imaging system comprising:
a) a pulsing x-ray source operable to produce selectively x-rays with one or more energy spectra
b) a linear array x-ray imaging device operable to produce x-ray imaging frames
c) one or more mechanical stages operable to move at least one of i) the x-ray source, ii) the linear array x-ray imaging device, iii) object or objects to be imaged, iv) a primary or secondary collimator,
   wherein said linear array x-ray scanning imaging system produces trigger pulses synchronized with at least one of 1) said pulsing x-ray source and 2) said mechanical stages, wherein
   said trigger pulses are tagging said frames produced by the linear array x-ray imaging device.

In further embodiments, said tagged frames are shifted and added on the application specific integrated circuit(s), which is coupled to the detector substrate for detecting incoming x-rays, comprising said linear array imaging device, to produce a Time Delay Integration ("TDI") output image stream.

In further embodiments, said TDI image stream is synchronized to the scanning speed.

In further embodiments, said TDI image stream comprises two separate TDI image streams one for each energy spectrum, composed from shifting and adding tagged frames from a first x-ray energy spectrum and providing said first image stream, shifting and adding tagged frames from a second x-ray energy spectrum and providing said second image stream.

In accordance with another aspect of the invention we provide a linear array x-ray imaging device, comprising:
a. a detector for detecting impinging x-rays and generating detector output signals;
b. an application specific integrated circuit, suitable for producing a frame output, for receiving said detector output signals and comprising a readout pixel array and electronics for producing digital output pixel values corresponding to a primary frame rate and a primary frame period;
wherein
said application specific integrated circuit further comprises a digital memory for storing a resulting digital pixel value from accumulation or averaging of digital output pixel values from at least two primary frame periods prior to readout of said resulting digital pixel value from said application specific integrated circuit and therefore outputting secondary frames with an effective frame rate that is slower than the primary frame rate and a secondary frame period which is longer than said primary frame period.

In certain embodiments, said secondary frames are tagged with external trigger signals synchronized with a) kV energy of a pulsing x-ray source and/or one of b) position, speed of the object under examination, said linear imaging device, x-ray source, primary or secondary collimator.

Different non-binding example aspects and embodiments have been presented in the foregoing. The above embodiments and embodiments described later in this description are used to explain selected aspects or steps that may be utilized in implementations of the present invention. It should be appreciated that corresponding embodiments apply to other example aspects as well. Any appropriate combinations of the embodiments can be formed.

In accordance with certain aspects, a provided linear array x-ray imaging device is single photon sensitive, operates in frame output mode and includes a pixel array Application Specific Integrated Circuit including the readout pixel array and on the same ASIC there is also provided digital control logic and sufficient digital memory to accumulate digital output frames in various modes of operation prior to output from the ASIC. In this way a number of advanced imaging functionalities are achieved directly on the ASIC such as static frame modulation, dynamic frame modulation and time delay integration output, while maintaining a very large dynamic range of 16 bits and single photon sensitivity. Furthermore, the effective or secondary frames that are output from the pixel array ASIC can be tagged with user provided external triggers synchronizing the effective frames to the x-ray beam energy and/or to the movement of the x-ray source or object to be imaged. This enables dual energy imaging and ultra-fast scanning, without the complexity and cost of conventional photon counting x-ray imaging sensors. The system architecture is simpler and achieves optimal imaging performance. Preferably the ASIC is a CMOS. Preferably the detector is of the direct conversion type, such as CdTe or CdZnTe; preferably CdTe with Al Schotky pixel structure.

Furthermore, in accordance with certain aspects, a provided CdTe (or CdZnTe) x-ray imaging device includes switching high voltage circuitry for depolarizing the CdTe detector. In certain embodiments, the high voltage is switched from an operational value to low voltage value of the same polarity in a very short period of time, such as 5 micro seconds. This removes the temporal behavior of CdTe and simplifies its calibration.

BRIEF DESCRIPTION OF THE DRAWINGS

In the following, the invention is presented in detail by referring to the attached drawings, where.

DETAILED DESCRIPTION

With reference now to the accompanying figures we describe in detail the invention and the preferred embodiments.

Figure 1:
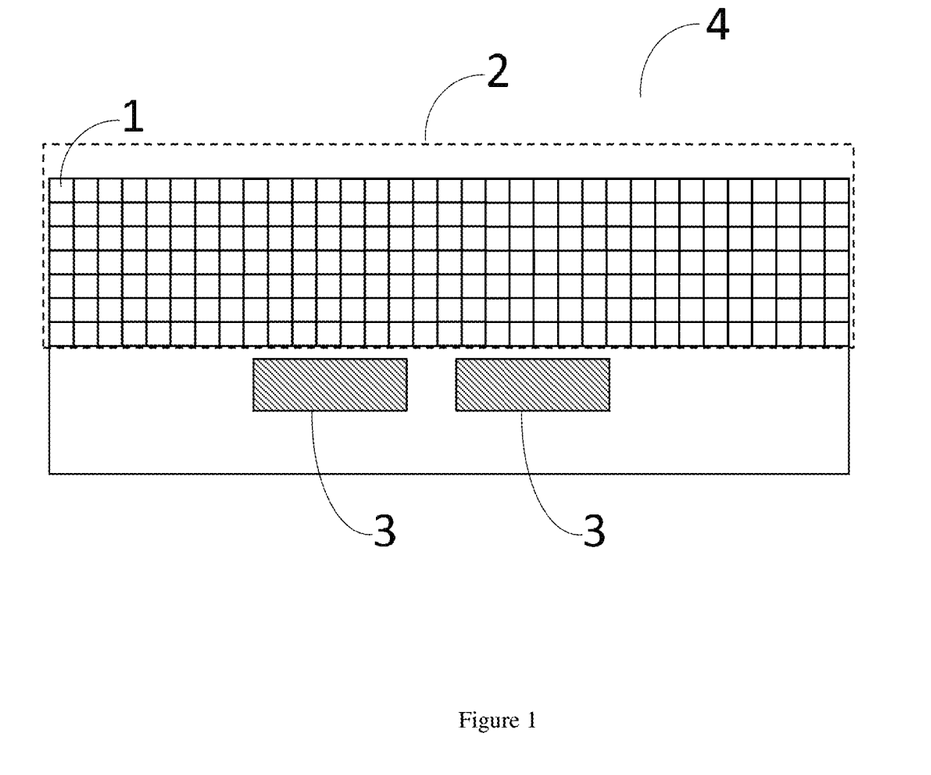
FIG. 1 shows schematically an application specific integrated circuit for x-ray imaging in accordance with certain embodiments.

With reference now to FIG. 1 an pixel array Application Specific Integrated Circuit ("ASIC") 4 is shown suitable for x-ray imaging in linear array ultra-fast scanners in accordance with the certain embodiments. The pixel array ASIC is preferable a CMOS, but other process possibilities are available. The ASIC 4 contains a pixel array 2. Each pixel 1 in the pixel array 2, in an indirect conversion sensor, is meant to detect light from the scintillator, therefore it has a photodiode on each pixel. Alternatively, and preferably the ASIC 4 is of the kind suitable for direct conversion x-ray imaging and each pixel collects charge or electric pulses. The pixels 1 at the pixel array 2 have circuitry for integrating the incoming charge (charge integration ASIC) (prior art) or for counting pulses corresponding to individual x-rays (photon counting ASIC) (prior art). However, additionally and in accordance with the certain embodiments the pixel array ASIC 4 includes also a digital memory block 3, which is functionally outside the pixel array, i.e. a memory that is able to receive and store frames as these come out from the pixel array and, importantly, such memory is an integral part of the CMOS comprising the actual pixel array. In other words, the entire imaging pixel array and the memory are part of the same monolithic CMOS. Emphasis is added that memory blocks 3 are resident on the very same ASIC that contains the pixel array that performs the x-ray imaging. External memory solutions are costly and have the issue that the data rate is too large to be transferred to the computer. Memories on the FPGA or the peripheral electronics in a printed circuit board or ceramic are a possibility but require more complex logic on the FPGA which again leads to a more complex architecture, more power consumption and bigger FPGA with more components. The imaging pixel array CMOS resident memory 3 is acting to simplify the overall architecture as will be explained. Furthermore memory 3, unlike prior art and in stark contrast is not (emphasis added) provided to store the frames produced by the pixel array 2 in a non-destructive manner, but quite contrary. Memory blocks 3 are provided to allow the incoming digital frames from the pixel array 2 to be processed by way of addition, accumulation or averaging in a number of ways and by doing so the original content of the individual frames is lost. The benefit is that one achieves optimal effective output frame rate, optimal data size, optimal speed while electronic noise, shot noise and white noise gets reduced due to the digital processing of multiple original frames. Furthermore, dynamic range is increased a lot since the pixels are readout fast and reset.

By way of example the pixel array primary frame rate may be as high as 10,000 fps with 100 um (hundred micrometers) pixel size in a linear sensor x-ray imaging scanning array of 230 mm×5.2 mm. At that frame rate the dynamic range is boosted to over $10^{}8$ x-rays/mm$^{}$2/sec (one hundred million x-rays per square millimeter per second) suitable for most x-ray imaging applications. However, at that frame rate the necessary bandwidth to transfer the data to a PC would be 14.3 Gbps, something not possible with any of the available ethernet protocols. Even if these data would somehow arrive to the computer it would be impossible to process it in real time. One could output the data from the pixel array CMOS to the FPGA on the sensor board and peripheral memory, but as explained earlier this increase cost and complexity. The essence in certain embodiments of the invention is that the memory block as part of the pixel array CMOS allows for the data rates to be reduced to reasonable levels and as required by the application. To keep the cost down and for simplicity and space requirements the on-chip memory is sufficiently small, and the primary frames are added up in a destructive manner or shifter and added in the case of a Time Delay Integration output ("TDI"). The resulting secondary frames have a slower rate and a larger corresponding effective frame period.

Figure 2:
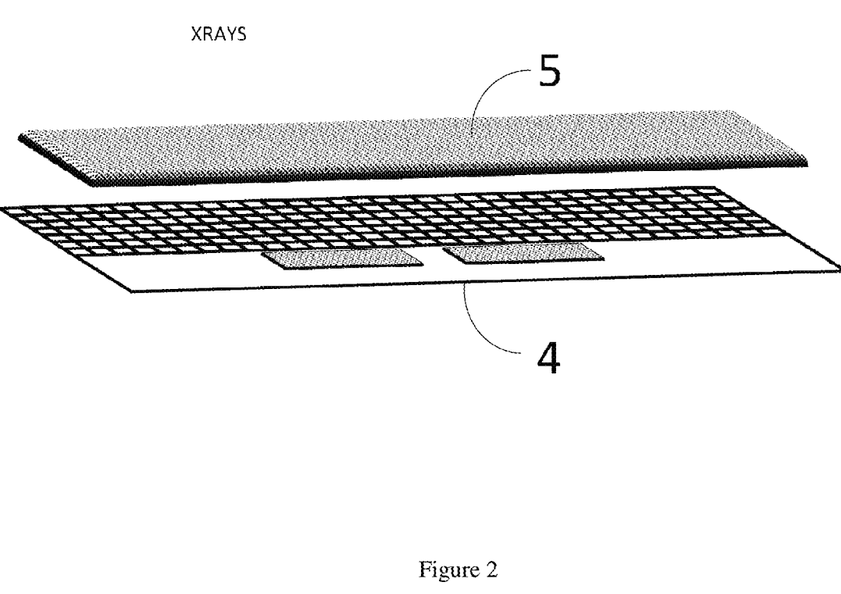
FIG. 2 shows schematically a detector in combination with an application specific integration circuit in accordance with certain embodiments.

Turning to FIG. 2 we show schematically the complete x-ray imaging device including the detector 5 and the readout ASIC 4. The detector 5 can be a scintillator like CsI or a phosphor which is glued to the ADIC using an optically transparent epoxy. Alternatively, and preferably it is of the direct conversion type such as CdTe, CdZnTe, GaAs, Ge, HgI$_2$, Si and Se. These direct conversion semiconductors can be single crystal formed and bump bonded to the ASIC or can be polycrystalline formed and deposited on the ASIC instead. The interconnections are not shown in FIG. 2.

Figure 3:
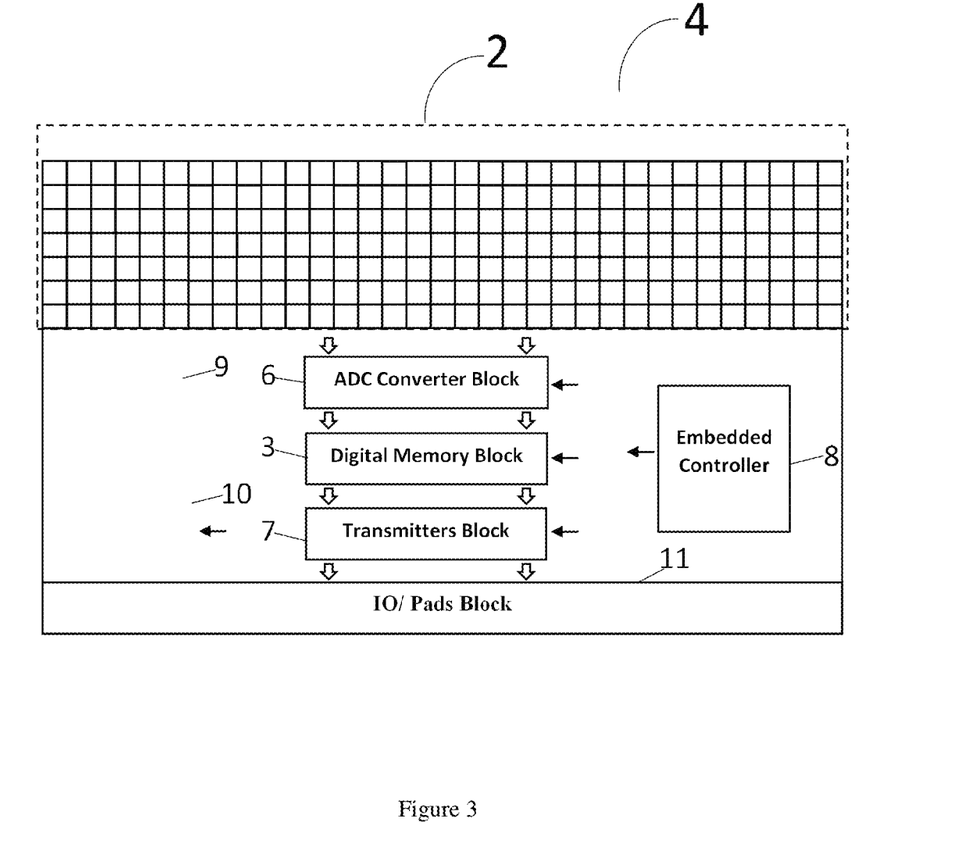
FIG. 3 shows a block diagram of the functional blocks of an application specific integrated circuit used in x-ray imaging in accordance with certain embodiments.

Turning to FIG. 3 the ASIC's main blocks are the Initialization Registers 10, used to store the settings that define the ASIC operation, through the Frames. They are accessible from the External controller (FPGA) through a custom SPI protocol. The two-dimensional pixel array 2 which consists of pixels 1. The pixel array is split in two parts in order to achieve higher frame rates. The ASIC also provides the feature to disable specific number of pixel rows in the pixel array, making the active area adjustable. This feature provides compatibility with detectors 5 of active areas with different width. The Analog to Digital Conversion ("ADC") block 6 is used to convert the analog values of the pixel 1 data to digital format. The resident ADC block can from 8 bits to 14 bits. If the ASIC is of the photon counting mode then the output from pixel array 2 is already digital and the ADCs can be omitted. Two ADC converters 6 are operating in parallel, one for each part. The digital memory block 3 which consists of two memory cells used for the pixels' data storage, implementing the accumulation of the pixels' data throughout the frames. The transmitters block 3 which is used to serialize the data from the memories and to transmit the data to the external controller FPGA. The DAC block 9 which is used to generate the required bias voltages and currents, for the proper operation of the analog circuits of the ASIC. The embedded controller 8 which is the coordinator of the ASIC and it communicates with the external controller (FPGA), it controls the initialization registers 10, coordinates the pixel array 2 phases of operation and controls the modules that are participating in the readout chain. The communication of the ASIC and the outside world is done through the I/O PADS block 11.

Figure 4:
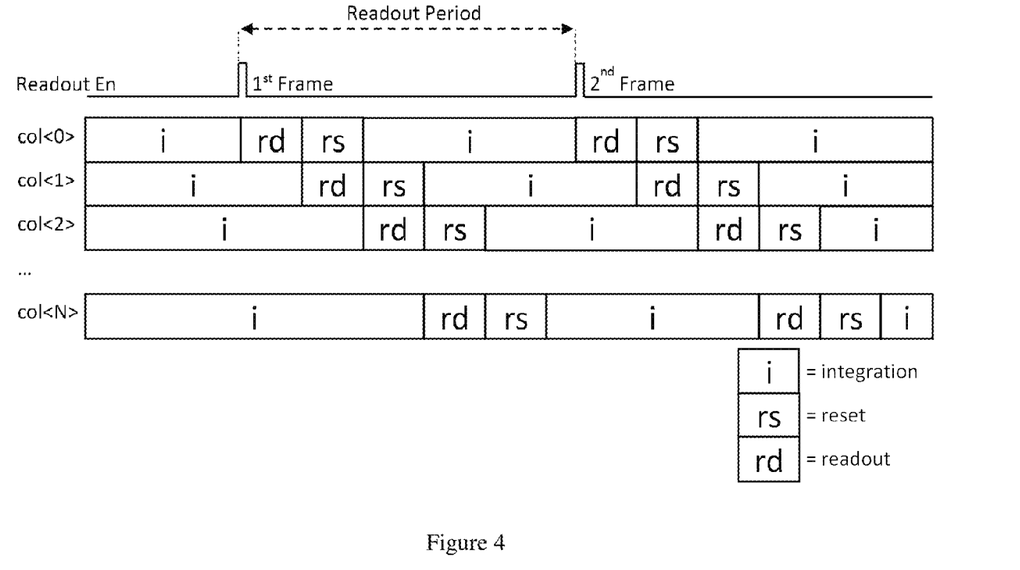
FIG. 4 shows the operational phases of the pixel array in an application specific integrated circuit in accordance with certain embodiments.

Turning to FIG. 4 the Operation Phases of the pixel array 2 are initiated by the external controller (FPGA) by asserting the "Readout Enable" signal. Once this external signal is asserted, it is sampled by the embedded controller 8 which signals the beginning of the readout phase of the pixel array 2. During this phase the pixels 1 are outputting their data sequentially pixel by pixel, column by column. Once the readout of one column finishes, this specific column will enter the reset phase where the input node will be reset to the reference voltage and this operation will continue until all the columns of the pixel array 1 are read out. After the reset phase which lasts for time equal to the readout time of 1 column the pixels 1 of the column enter the integration phase in which the current pulses arriving at its input are integrated for the rest of the frame until the new "Readout Enable" signal arrives and the new Frame begins. This defines the frame period or otherwise known as frame duration, which is the period during which the pixels integrate the x-ray content that arrives before readout. The frame duration which defines the frame rate and thus the integration time can be adjusted by changing the Readout period between the sequential "Readout Enable" signals. In steady frame modulation the user predefines how many primary frames he wishes to accumulate on the on-chip memory prior to outputting a secondary or effective frame. For example, if the primary readout period "i" is 100 usec it corresponds to a primary frame rate of 10,000 fps. Accumulating on the pixel array CMOS ×2 frames yields an effective (secondary) frame rate of 5,000 fps; ×3 accumulation yields 3,333 fps and so on. In the preferred implementation the primary frame rate is between 1,000 fps and 10,000 fps and the on the pixel array CMOS memory one accumulates from 2 to up to 255 primary frames for generating an effective or secondary frame output between 4 fps to 1,000 fps. The bit resolution of the primary frames is preferably 12 bits (FIG. 5; ADC 6) as defined by the on-chip ADC. The maximum bit depth of the effective frames is up to 20 bits and in accordance with certain embodiments the 4 least significant bits are then dropped for an effective output of 16 bits which is indeed an extremely high resolution.

Figure 5:
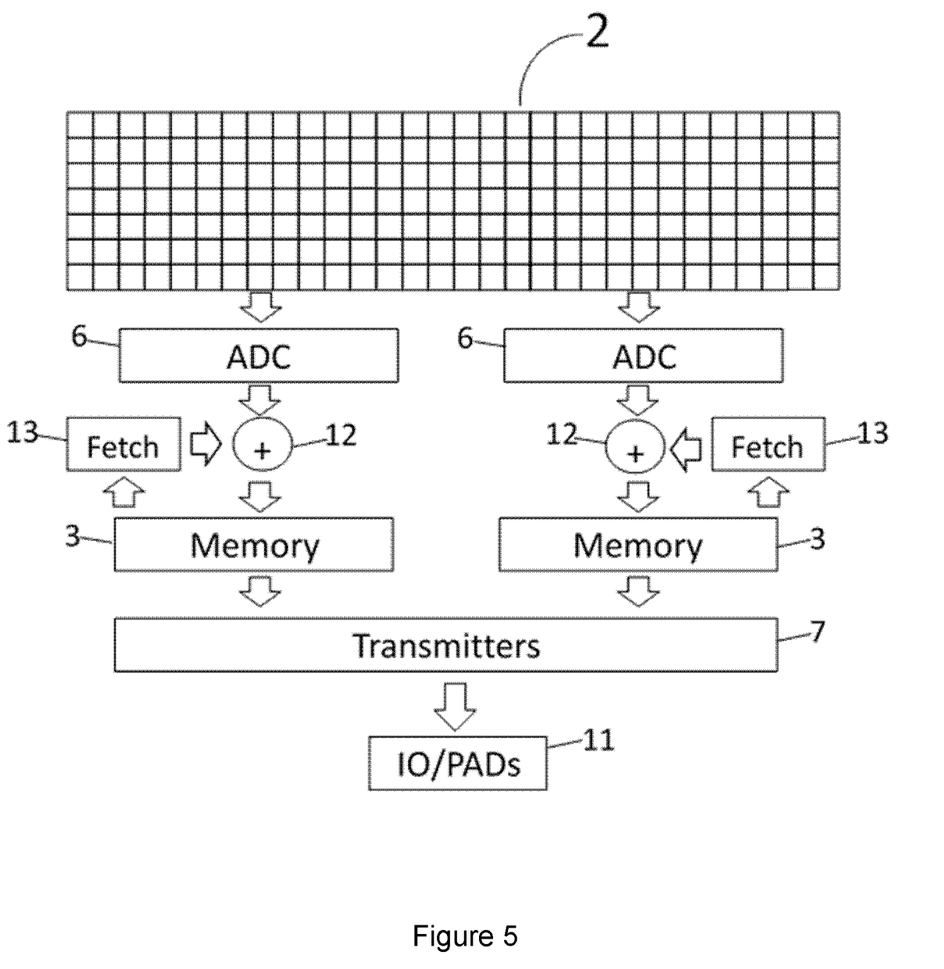
FIG. 5 shows a block diagram of the digital functionality of the application specific integrated circuit in an x-ray imaging device in accordance with certain embodiments.

Turning now to FIG. 5 the scheme used for the dynamic frame modulation is shown here. The pixels 1 in the pixel array 2 are outputting their data sequentially one by one. The user sets in the initialization registers 10 the required number of frames which needs to be accumulated. Once set, the operation of the ASIC starts and at the first frame the pixels 1 in the pixel array 2 are outputting their analog data sequentially one by one, while the pixel array 2 is read with a fixed readout period. The ADC converters 6 are digitizing the analog values of the pixels 1 which are then stored in the digital memories 3 in unique memory addresses for each pixel. On the next frames the digitized pixels' data that are stored in the digital memory 3 are fetched using a circuit 13 and by using adders 12, the pixels' data from the latest frame are added to the fetched data, which is the accumulated pixels' data from the previous frames. Once the number of the accumulated frames is equal to the required number of frames, the embedded controller signals the readout of the accumulated data which are then sent to the external controller (FPGA) using the transmitters' block 7. By keeping the pixel array 2 readout period constant and by changing dynamically the required number of frames to be accumulated, the dynamic frame modulation can be achieved, without compromising the frame rate of the initial or primary frames. As discussed earlier this is very advantageous because the dynamic range is very high since the pixels are very fast readout and reset and the electronic noise is reduced a lot. For example by adding or averaging in static or dynamic frame modulation the KTC, shot and white noise even out as in a low pass filter. Furthermore the printed circuit board design, FPGA design and peripheral component placement is greatly simplified and cost is reduced. As can be realized from the above description the frames 2 coming out from the pixels, i.e. the CMOS imaging device are destructively stored in the memory blocks 3 that is resident on the very same ASIC CMOS that performs the imaging operation.

Figure 6:
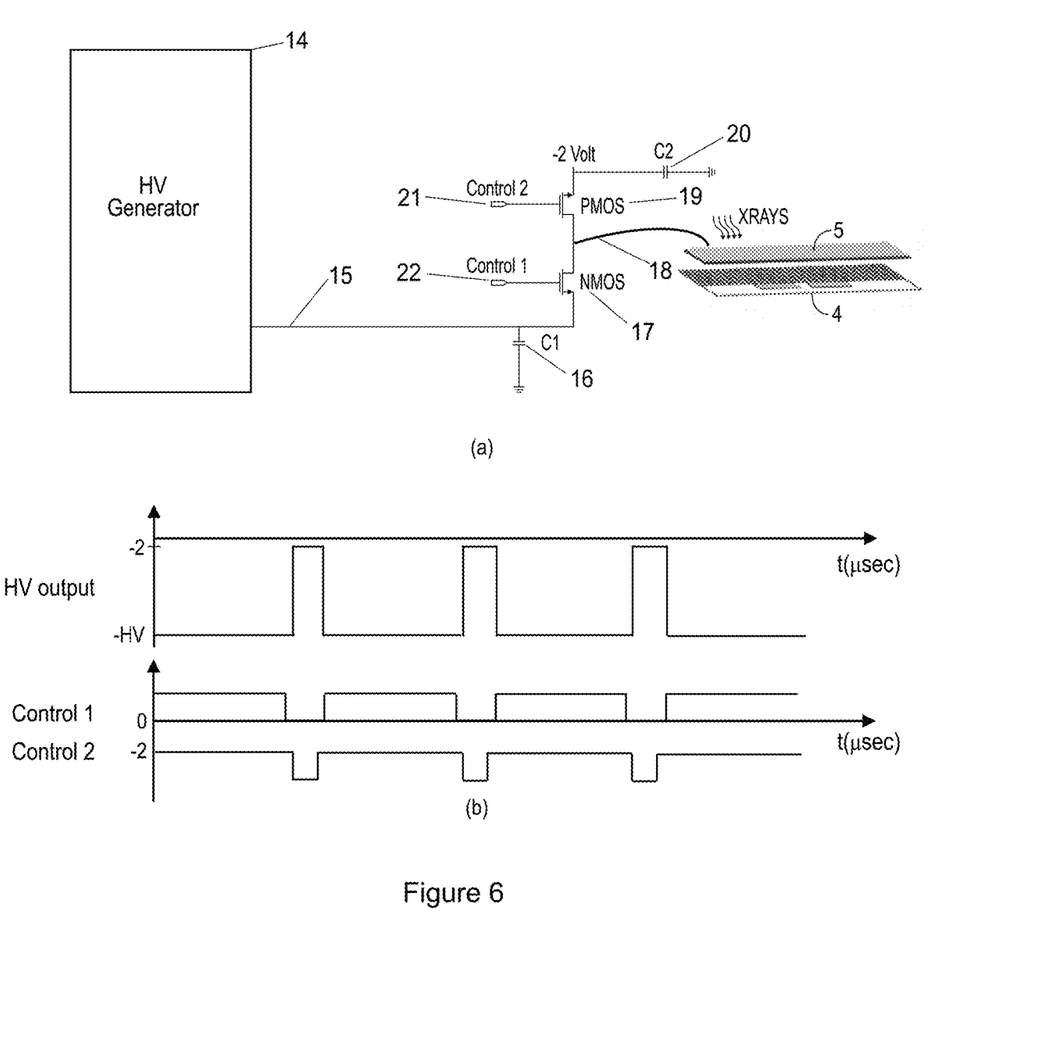
FIG. 6 shows a very fast switching High Voltage circuit and arrangement for depolarizing a CdTe x-ray imaging device in accordance with certain embodiments.

Turning now to FIG. 6 we present the switching high voltage circuit arrangement for depolarizing the CdTe or CdZnTe or other direct conversion detectors. The ultra-fast high voltage switching, and its operating timing diagram is shown. In the preferred embodiment of FIG. 6, the HV Generator 14 is generating a negative bias voltage typically −200 V to −500 V in the case of CdTe with Al Schotky on the pixel side and its output 15 is charging the capacitor C1 16. The polarity however of the high voltage can be reversed as necessary depending on the detector type. At the same time the transistor NMOS 17 is activated and the switch is said to be in the ON state by shorting the output 15 to the high voltage wire 18, providing the required bias voltage to the detector 5. When a bias refresh is needed then the switch consisting from the two transistors 17, 19 and the two capacitors 16, 20 switches the high voltage wire 18 from the ON state to the OFF state and finally back to the ON state again. The whole bias refresh operation may last for 5 μs or 20 μs or 100 μs or 500 μs or 1 ms. Most preferably the smallest possible ON/OFF time is implemented that provides stable performance, i.e. removing the polarization and temporal response with optimal minimum loss of frame integration time. During the ON to OFF switching the transistor NMOS 17 is deactivated and after a few nanoseconds the transistor PMOS 19 is activated, driving the high voltage wire 18 to −2 Volt. The switching from the negative bias voltage to the −2 Volt is done rapidly with the aid of the capacitor C2 20 which provides the required current without overloading the voltage source generating the −2 Volts.

During the OFF to ON state switching, the transistor PMOS 19 is de-activated and after a few nanoseconds the transistor NMOS 17 is activated and with the aid of the capacitor C1 16 which feeds the extra current without overloading the HV Generator 14, the switching back to the negative bias voltage is done rapidly. The bias refresh takes place every 10000 frames, more preferably every 1000 frames, even more preferably every 100 frames or every 1 frame. The ON/OFF short period of time and frequency of applying it, i.e. periodic time intervals can be suitably optimized to achieve a) minimum loss of frame integration time, b) mitigation of polarization and temporal behavior of the detector and c) continuous operation in an x-ray imaging environment.

Figure 7:
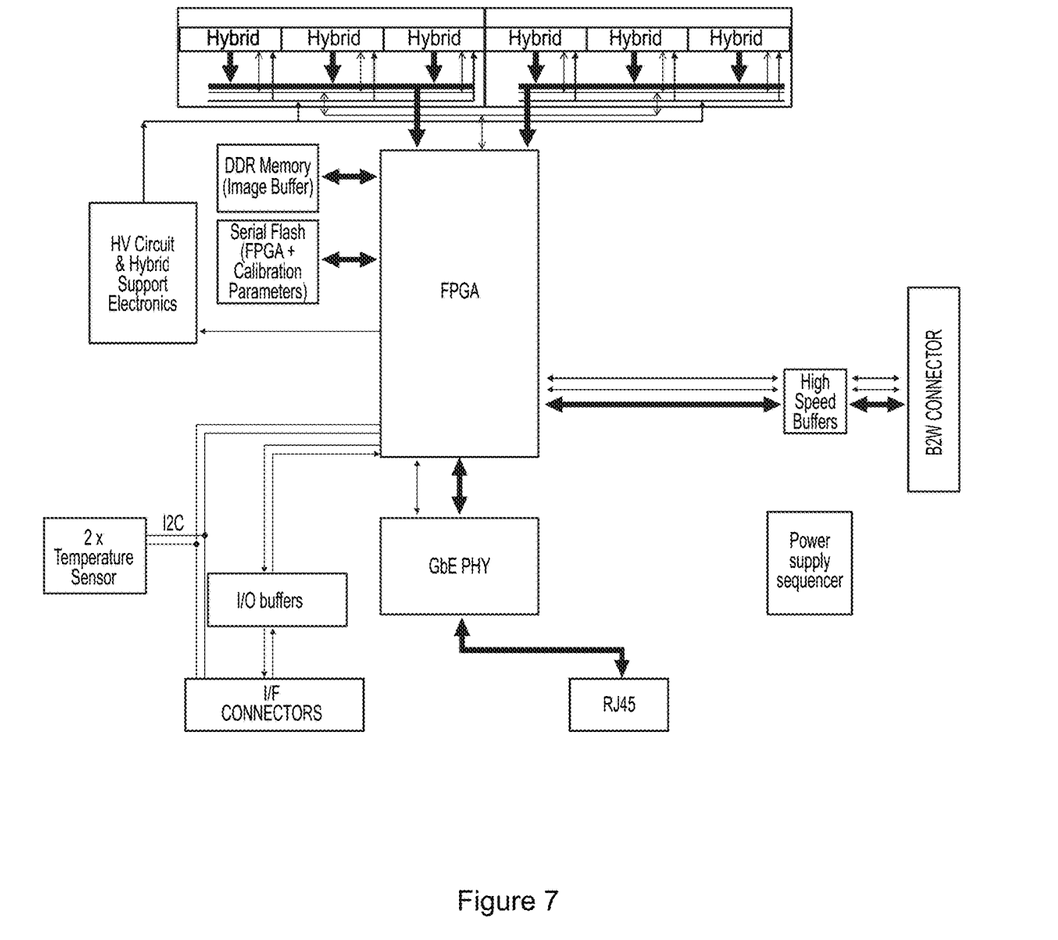
FIG. 7 shows a block diagram of the linear array x-ray imaging device according to certain embodiments.

FIG. 7 shows a block diagram of the entire linear array x-ray imaging device according to certain embodiments. FIG. 7 shows six hybrids by way of example. A hybrid is referred to as the CdTe detector bump-bonded to the pixel array ASIC. Each hybrid is preferably 15 mm-30 mm long and 3 mm-6.5 mm wide. The pixel size is preferably between 50 um to 200 um; most preferably 100 um. The pixel array ASIC functionality has been described in detail in the previous sections and Figures. The sensor board includes an FPGA (Field Programmable Gate Array) which controls the pixel array ASICs (typically of the CMOS type), a DDR memory for temporarily storing the effective frames produced by the pixel array ASICs, a flash memory for storing on the actual sensor board the calibration and other parameters, the HV circuit generating the high voltage and the HV switching circuitry for switching the HV in order to keep the CdTe stable. In accordance with certain embodiments, the effective (or secondary) frames, with a frame rate lesser than the primary frame rate produced on the pixel array ASICs, are temporarily stored on the DDR. The DDR may be 4 Gbit fitting easily 3,000 frames at 12 bit depth from a 230 mm long linear scanner, 4 mm wide. The user or application system can issue external triggers which are going through the I/F connectors and via the I/O buffers to the FPGA. The FPGA then is able to use such triggers to actually determine when and at what rate effective (or secondary) frames are coming out from the pixel array ASICs, achieving steady effective frame rate, dynamically modulated during the exposure effective frame rate or TDI on the pixel array ASIC. These effective frames then can be tagged and synchronized with a pulsing x-ray source switching its energy between two different kV settings, a mechanical stage or both. The frames in addition to be tagged with external "energy" and "speed" triggers can be further shifted and added inside the FPGA creating video or image streams;

each stream corresponding to a set of triggers. In this way dual energy imaging is possible. For example, when the primary frame rate is 10,000 fps, external pulsing x-ray source triggers can create, two TDI streams coming out of the pixel array ASIC, each at 50 cm/sec and each corresponding to the specific kV setting of the pulsing x-ray source. Alternatively, the frames come out from the pixel array ASIC at 10,000 fps and then shifted and added as well as tagged with external triggers inside the FPGA.

Figure 8:
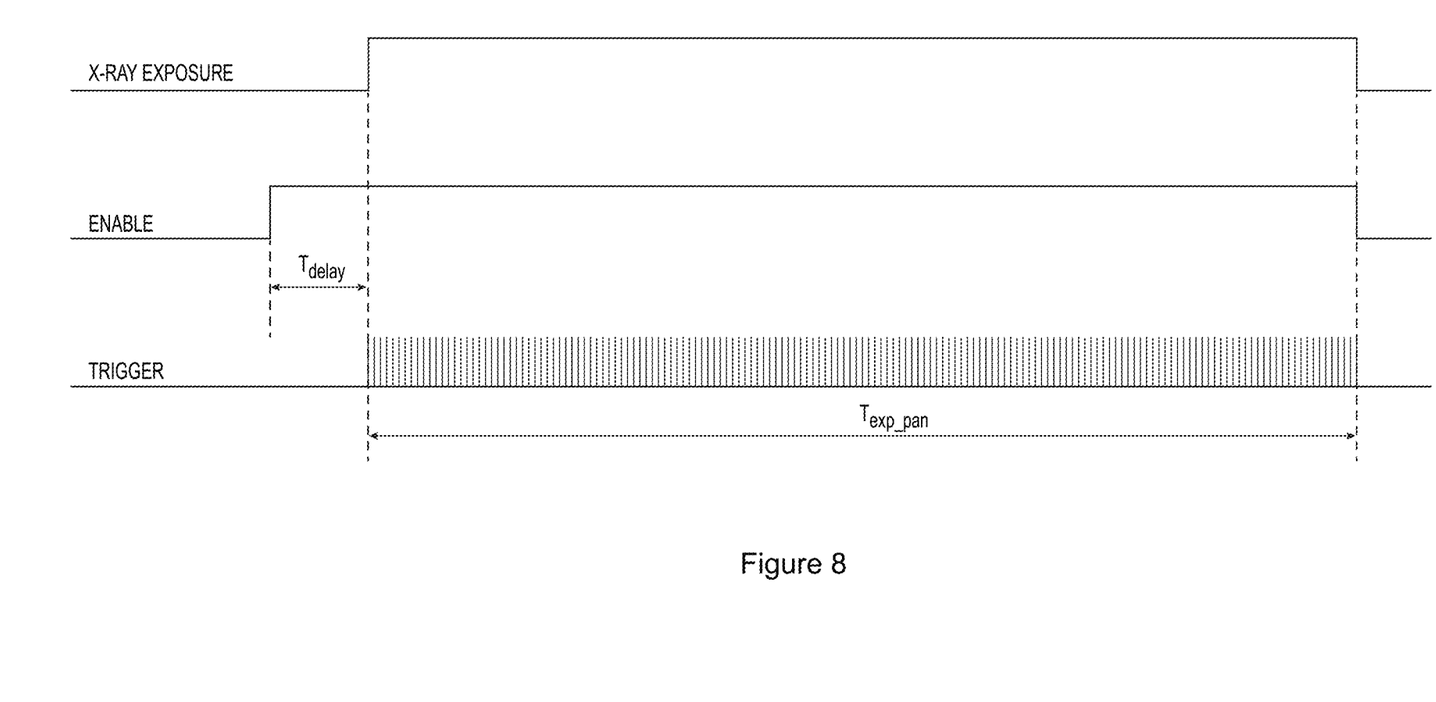
FIG. 8 shows the external triggers that are at the disposal of the user and/or system to synchronize the linear array x-ray imaging device in certain embodiments.

FIG. 8 shows by way of example one such triggering scheme. At time $T_{delay}$ prior to the start of the x-ray exposure the linear array sensor is initiated. During exposure a master clock of for example 20 MHz to 50 MHz continuously produces primary frames at very high rate on the linear array ASIC. Such primary rates are from 1,000 fps to 10,000 fps or more with 100 um pixel resolution and linear scanner lengths of few cm and up to 100 cm long. The primary frames are digitized on the pixel array ASIC and then stored on the memory available on the pixel array ASIC and continuously added to the existing stored primary frames until a modulation step sequence or "TRIGGER" signals as shown instruct the digital controller on the pixel array ASIC to output a secondary frame (steady secondary frame rate or dynamic secondary frame modulation) or shift and add the next primary frame and output a TDI stream. These same modulation steps can be used to tag the effective or secondary frames timewise to certain external system parameters (moving stages) or energy wise (pulsing x-ray source). As mentioned earlier up to 255 primary frames can be added on the pixel array ASIC memory or shifted and added and then output as lines.

The foregoing description has provided by way of non-limiting examples of particular implementations and embodiments of the invention a full and informative description of the best mode presently contemplated by the inventors for carrying out the invention. It is however clear to a person skilled in the art that the invention is not restricted to details of the embodiments presented above, but that it can be implemented in other embodiments using equivalent means without deviating from the characteristics of the invention.

Furthermore, some of the features of the above-disclosed embodiments of this invention may be used to advantage without the corresponding use of other features. As such, the foregoing description should be considered as merely illustrative of the principles of the present invention, and not in limitation thereof. Hence, the scope of the invention is only restricted by the appended patent claims.

The invention claimed is:

1. A linear array x-ray scanning imaging system comprising:
a) one or more x-ray sources configured to produce selectively x-rays with a first and a second energy spectrum,
b) a linear array x-ray imaging device configured to produce x-ray imaging frames,
wherein said linear array x-ray scanning imaging system is configured to produce a first trigger pulse synchronized with said first energy spectrum and a second trigger pulse synchronized with said second energy spectrum and said first and second trigger pulses are configured to tag said frames produced by the x-ray imaging device.

* * * * *